US00PP08039P

United States Patent [19]

Zaiger et al.

[11] Patent Number: Plant 8,039

[45] Date of Patent: Nov. 24, 1992

[54] NECTARINE TREE "AUGUST GLO"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 710,150

[22] Filed: Jun. 4, 1991

[51] Int. Cl.[5] ..... A01H 5/00

[52] U.S. Cl. ..... Plt./41.1

[58] Field of Search ..... Plt./41

*Primary Examiner*—James R. Feyrer

[57] ABSTRACT

A new and distinct variety of nectarine tree which has the following unique combination of desirable features:

1. Late maturity of fruit.
2. Fruit with good flavor and eating quality.
3. Vigorous upright growth.
4. The ability of bear relatively uniform sized fruit with very heavy production.
5. Large size of yellow flesh clingstone fruit.
6. Fruit with firm flesh, good storage and shipping qualities.
7. Fruit with bright yellow ground colored skin, overspread with an attractive red blush.

1 Drawing Sheet

ORIGIN OF THE VARIETY

The new and distinct nectarine variety was originated by us in our experimental orchard as a first generation cross between two selected seedlings with the identification numbers 60G342 and 33EA230. The selected seedling with the identification number 60G342, which is the female parent, originated from a second generation seedling from a cross between Sun Grand Nectarine (U.S. Plant Pat. No. 974), and Merril Gem Peach (U.S. Plant Pat. No. 868). The pollen parent with the identification number 33EA230 was selected as a second generation seedling from a cross between a nectarine selection of unknown parentage and August Grand Nectarine (U.S. Plant Pat. No. 2,894). A large group of seedlings from this cross were planted and grown in our experimental orchard located near Modesto, Calif. One such seedling which represents the present variety, having especially desirable fruit characteristics was selected for asexual reproduction and commercialization.

ASEXUAL REPRODUCTION OF THE VARIETY

The present variety of nectarine tree was asexually reproduced by budding, as performed by us, in our experimental orchard located near Modesto, Calif., and shows that all characteristics come true to the original tree and are established and transmitted through succeeding propagations.

SUMMARY OF THE VARIETY

The new and distinct variety of nectarine tree is of large size, vigorous upright growth and is a productive and regular bearer of large size, firm, yellow flesh, clingstone fruit with good flavor and eating quality. The fruit is further characterized by being relatively uniform in size throughout the tree, having good storage and shipping qualities and in comparison to Autumn Grand Nectarine (U.S. Plant Pat. No. 2,894) the new variety has the ability to produce more uniform size of fruit with a higher degree of attractive red skin blush and to ripen approximately 10 days eariler.

PHOTOGRAPH OF THE VARIETY

The accompanying color photograph shows reproductions of the foliage and fruit of the new variety of nectarine tree. The illustrations are of the upper and lower surface of the leaves, the exterior and sectional view of the fruit divided in the suture plane to reveal flesh coloration and showing a stone remaining in place. The photographic illustrations were taken shortly after being picked (firm ripe) and the colors are as nearly true as reasonably possible in a color representation of this type.

DESCRIPTION OF THE VARIETY

The following is a botanically detailed description of the new nectarine tree, its flowers, foliage and fruit as based on observations of the specimens grown near Modesto, Calif., with color terminology (except those in common terms) in referenced to Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Production.*—Very productive.
- *Bearer.*—Regular.

Trunk:
- *Size.*—Large.
- *Texture.*—Medium shaggy.
- *Color.*—Brown to grayish brown (5-E-4) to (5-E-5).

Branches:
- *Size.*—Medium.
- *Texture.*—Medium rough.
- *Lenticels.*—Numerous. Medium size.
- *Color.*—Reddish brown to brown (8-E-3) to (8-E-6).

Leaves:
- *Size.*—Large. Average length — 6" to 6¾". Average width — 1½" to 1¾".
- *Margin.*—Crenate.
- *Petiole.*—Medium length. Medium thickness.

*Glands.*—Globose. Medium size. Number varies from 1 to 5. Average number 3. Located on lower portion of leaf blade and the upper portion of the petiole.

*Form.*—Lanceolate.

*Color.*—Upper surface — light green to green (29-E-8) to (29-F-7). Lower surface — light green to dull green (29-E-6) to (29-E-7).

Flower buds:

*Size.*—Medium to large.

*Form.*—Plump.

*Pubescence.*—Pubescent.

Flowers:

*Size.*—Large — showy.

*Blooming period.*—Mar. 1, 1990 to Mar. 8, 1990. Varies slightly with climatic conditions.

*Pollen.*—Present. Self fertile.

*Color.*—Pink.

Fruit:

*Maturity when described.*—Firm ripe.

*Date of first picking.*—Aug. 10, 1990.

*Date of last picking.*—Aug. 17, 1990.

*Size.*—Large. Average diameter axially — $2\frac{3}{4}''$. Average transversely in suture plane — $2\frac{3}{4}''$.

*Form.*—Nearly globose.

*Suture.*—Shallow — extends from base to apex.

*Ventral surface.*—Very shallow — nearly round.

*Cavity.*—Rounded to slightly elongated in suture plane. Average depth — $\frac{1}{2}''$. Average breath — $\frac{3}{4}''$.

*Base.*—Retuse.

*Apex.*—Usually slight point, varies from slight point to slight depression.

Flesh:

*Ripens.*—Evenly.

*Texture.*—Firm, meaty.

*Juice.*—Moderate.

*Fibers.*—Medium size, tender.

*Aroma.*—Moderate.

*Eating quality.*—Good.

*Flavor.*—Mild, good balance between acid and sugar.

*Color.*—Varies from light yellow to pale orange (4-A-4) to (5-A-4). Pit cavity varies from red to cherry red (10-A-7) to (10-B-8).

Skin:

*Thickness.*—Medium.

*Texture.*—Medium tough; tenacious to the flesh.

*Tendency to crack.*—None.

*Down.*—Wanting.

*Color.*—Yellow ground color (4-A-7) to (5-A-7). Red blush covering most of the surface of the fruit, light red to red (9-A-7) to (9-B-7).

Stone:

*Type.*—Clingstone; adheres to flesh over entire surface.

*Size.*—Large. Average length — $1\frac{5}{8}''$. Average breadh — 1 1/16″. Average thickness — $\frac{5}{8}''$.

*Form.*—Oval, elliptic.

*Base.*—Usually straight — some stones rounded.

*Apex.*—Cuspidate — small to medium size.

*Sizes.*—Mostly equal.

*Surface.*—Furrowed toward apex, pitted toward base. Pits elongated to round shape.

*Tendency to Split.*—Very slight.

*Color.*—Reddish brown to brownish red (10-D-5) to (10-D-7).

Use:

*Markets.*—Local and long distance shipments. Dessert.

Shipping Quality: Good.

Keeping Quality: Good.

The nectarine tree, its flowers and fruit herein described may vary in slight detail due to soil type, climatic conditions and cultural practices under which the variety may be grown; the present description is that of the variety grown under the ecological conditions prevailing near Modesto, Calif.

We claim:

1. A new and distinct variety of nectarine tree as illustrated and described, characterized by large size, vigorous upright growth; and a productive and regular bearer of yellow flesh, clingstone fruit with an attractive red skin blush; the fruit is further characterized by have good eating, storage and shipping qualities; and in comparison to Autumn Grand Nectarine (U.S. Plant Pat. No. 2,894) as having fruit with a greater degree of attractive red skin blush and maturing approximately 10 days earlier.

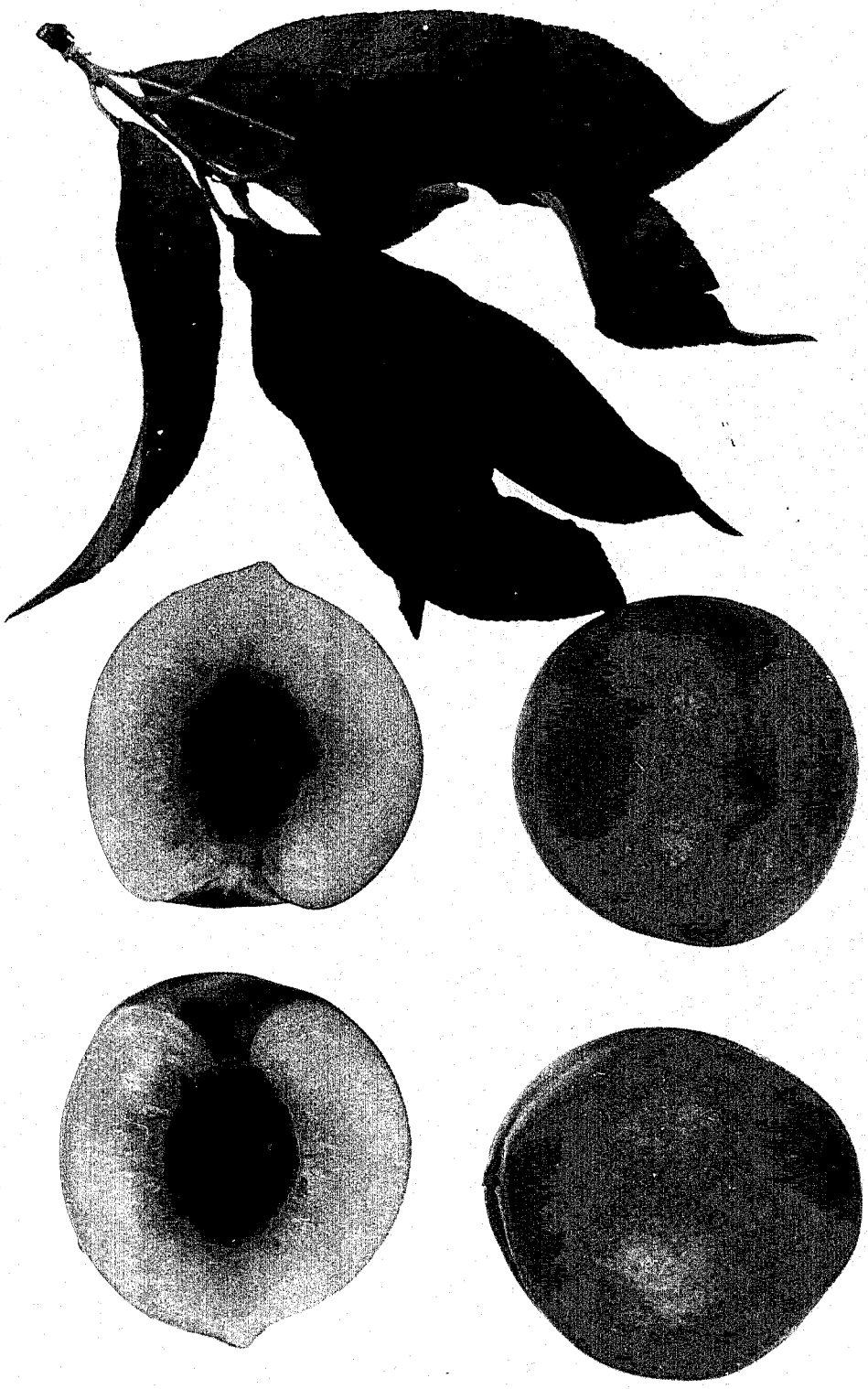

* * * * *